United States Patent
Stigall et al.

(10) Patent No.: US 11,890,136 B2
(45) Date of Patent: Feb. 6, 2024

(54) FLUID BARRIER FOR INTRALUMINAL ULTRASOUND IMAGING AND ASSOCIATED DEVICES, SYSTEMS, AND METHODS

(71) Applicant: KONINKLIJKE PHILIPS N.V., Eindhoven (NL)

(72) Inventors: Jeremy Stigall, Carlsbad, CA (US); Nathan Andrew Williams, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 634 days.

(21) Appl. No.: 16/539,210

(22) Filed: Aug. 13, 2019

(65) Prior Publication Data
US 2020/0060645 A1    Feb. 27, 2020

Related U.S. Application Data

(60) Provisional application No. 62/721,342, filed on Aug. 22, 2018.

(51) Int. Cl.
*A61B 8/00* (2006.01)
*A61B 8/08* (2006.01)
(Continued)

(52) U.S. Cl.
CPC .............. *A61B 8/12* (2013.01); *A61B 8/0891* (2013.01); *A61B 8/445* (2013.01); *A61B 5/6851* (2013.01);
(Continued)

(58) Field of Classification Search
CPC ......... A61B 8/12; A61B 8/0891; A61B 8/445; A61B 5/6851; A61B 8/4494;
(Continued)

(56) References Cited

U.S. PATENT DOCUMENTS 4,967,753 A    11/1990  Haase
6,357,447 B1   3/2002   Swanson et al.
(Continued)

FOREIGN PATENT DOCUMENTS

WO    1996034561 A1     11/1996
WO    WO-2017168290 A1 *  10/2017  ........... A61B 8/0883

*Primary Examiner* — Serkan Akar
*Assistant Examiner* — Amal Aly Farag

(57) ABSTRACT

Improved intraluminal imaging devices and methods of manufacturing the devices are provided. In an embodiment, an intraluminal imaging device can include a flexible elongate member configured to be positioned within a body lumen of a patient, the flexible elongate member comprising a proximal portion and a distal portion, an ultrasound scanner assembly coupled to and positioned distally of the distal portion of the flexible elongate member, the ultrasound scanner assembly comprising a plurality of electrical components disposed adjacent to a cavity of the ultrasound scanner assembly, and a coating extending over and directly contacting the distal portion of the flexible elongate member and a portion of the ultrasound scanner assembly to hermetically seal the cavity of the ultrasound scanner assembly. The coating provides a uniform barrier layer extending over a junction of two or more components having diverse cross-sectional profiles to prevent ingress of external fluids into the scanner assembly.

20 Claims, 8 Drawing Sheets

(51) Int. Cl.
  *A61B 8/12*     (2006.01)
  *A61B 5/00*     (2006.01)
  *B06B 1/02*     (2006.01)
  *B06B 1/06*     (2006.01)

(52) U.S. Cl.
  CPC ............ *A61B 8/4272* (2013.01); *A61B 8/4494* (2013.01); *B06B 1/0292* (2013.01); *B06B 1/0633* (2013.01)

(58) Field of Classification Search
  CPC ... A61B 8/4488; B06B 1/0292; B06B 1/0633; A61L 17/145; G01N 2030/185; G06T 2207/30021
  See application file for complete search history.

(56) References Cited

U.S. PATENT DOCUMENTS

| | | | |
|---|---|---|---|
| 6,776,763 B2 | 8/2004 | Nix et al. | |
| 7,226,417 B1 | 6/2007 | Eberle et al. | |
| 7,846,101 B2 | 12/2010 | Eberle et al. | |
| 2004/0044286 A1* | 3/2004 | Hossack | A61B 8/445 600/585 |
| 2006/0235314 A1 | 10/2006 | Migliuolo | |
| 2006/0251795 A1 | 11/2006 | Kobrin et al. | |
| 2007/0239024 A1 | 10/2007 | Eberle | |
| 2011/0062824 A1* | 3/2011 | Wada | B06B 1/0622 29/25.35 |
| 2014/0184026 A1 | 7/2014 | Reiter | |
| 2014/0257105 A1* | 9/2014 | Dausch | A61B 8/4281 600/458 |
| 2015/0305710 A1 | 10/2015 | Stigall et al. | |
| 2016/0066881 A1* | 3/2016 | Li | A61B 8/12 600/443 |

\* cited by examiner

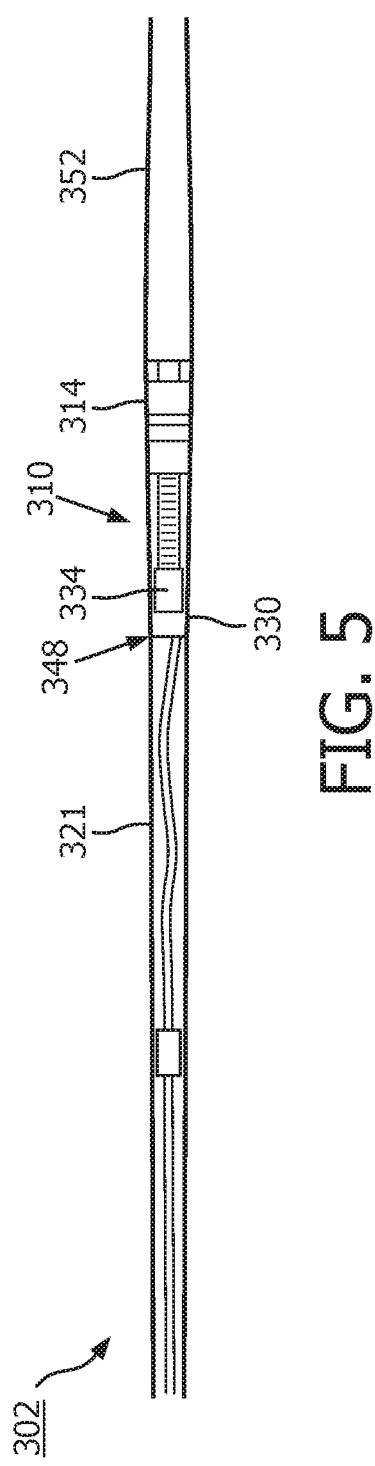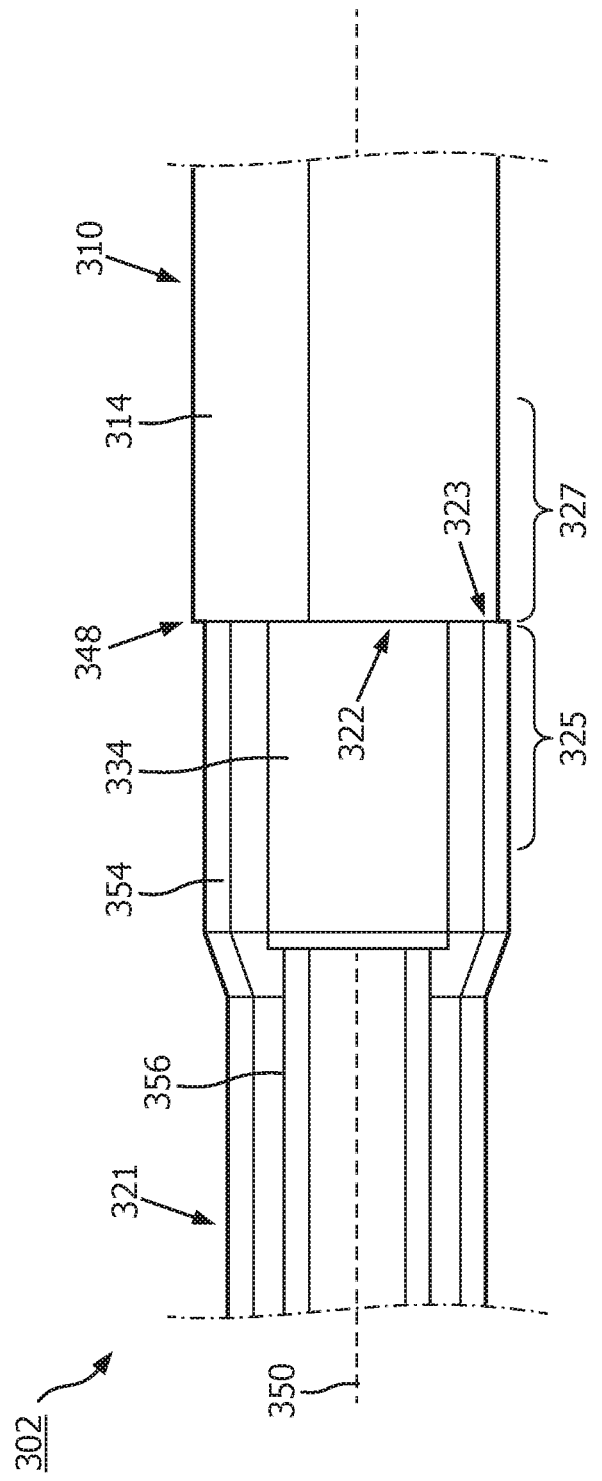

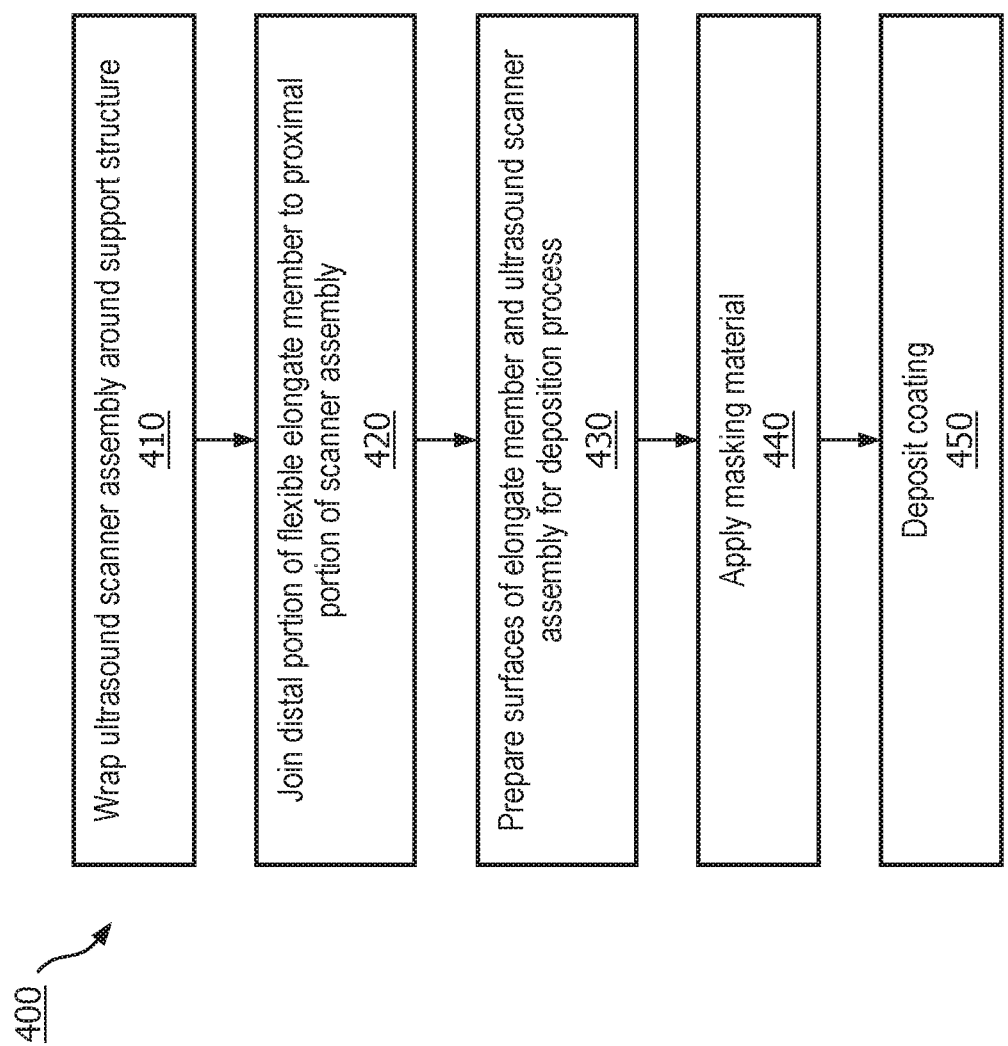

FLUID BARRIER FOR INTRALUMINAL ULTRASOUND IMAGING AND ASSOCIATED DEVICES, SYSTEMS, AND METHODS

CROSS-REFERENCE TO PRIOR APPLICATIONS

This application claims the benefit of U.S. Provisional Application No. 62/721,342, filed on 22 Aug. 2018. This application is hereby incorporated by reference herein.

TECHNICAL FIELD

The present disclosure relates generally to intraluminal medical imaging and, in particular, to the distal structure of an intraluminal imaging device. For example, the distal structure can include a flexible substrate that is rolled onto a support structure, joined to a flexible elongate member, and coated with a film to facilitate efficient assembly and operation of the intravascular imaging device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual acoustic elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing solid-state IVUS devices that can efficiently traverse anatomic structures within the human body is challenging. The devices must be sealed such that any sensitive electronic components (e.g., traces, conductors) do not come in contact with blood or fluids external to the devices. In that regard, discontinuities in the structures, such as gaps or interfaces between various components of the IVUS devices having diverse cross-sectional profiles can be difficult to fill or seal, while maintaining a small profile for the IVUS devices to efficiently traverse tortuous vasculature. Existing methods of using an adhesive fillet and/or a jacket layer to seal the IVUS device undesirably add complexity to the manufacturing process and/or increase the profile.

SUMMARY

Embodiments of the present disclosure provide improved intraluminal imaging devices and methods of manufacturing the devices that overcome the limitations described above. For example, an intraluminal imaging device can include a flexible elongate member joined to an ultrasound scanner assembly, and a coating positioned over and directly contacting the flexible elongate member and the ultrasound scanner assembly. The coating, which can be applied by a deposition process, provides a uniform barrier layer extending over a junction of two or more components having diverse cross-sectional profiles to prevent ingress of external fluids into the scanner assembly. The methods of depositing the coating, which may also be described as a film or thin film, may reduce the need for human intervention in the manufacturing and assembly process, and therefore reduce human errors and inconsistencies associated with other assembly and sealing processes. The film may also provide a barrier with desirable characteristics, such as a thin cross-sectional profile, biocompatibility, uniform thickness, and suitability for a variety of surfaces, shapes, and profiles.

According to one embodiment, an intraluminal imaging device includes a flexible elongate member configured to be positioned within a body lumen of a patient, the flexible elongate member comprising a proximal portion and a distal portion, an ultrasound scanner assembly coupled to and positioned distally of the distal portion of the flexible elongate member, the ultrasound scanner assembly comprising a plurality of electrical components disposed adjacent to a cavity of the ultrasound scanner assembly, and a coating extending over and directly contacting the distal portion of the flexible elongate member and a portion of the ultrasound scanner assembly to hermetically seal the cavity of the ultrasound scanner assembly.

In some embodiments, the coating is deposited directly over the distal portion of the flexible elongate member and the portion of the ultrasound scanner assembly. In some embodiments, the coating comprises a hydrophobic material. In some embodiments, the coating comprises parylene. The coating comprises a thickness of less than 3 microns, in some embodiments. In some aspects, the coating comprises a boundary formed by a masking line. In some embodiments, the coating is deposited around perimeters of the flexible elongate member and the ultrasound scanner assembly. In other aspects, the ultrasound scanner assembly comprises one or more acoustic elements, and the coating comprises an acoustic matching layer positioned over the one or more acoustic elements.

In some embodiments, the ultrasound scanner assembly comprises a flexible substrate including a proximal portion and a distal portion, and the flexible substrate is positioned around a longitudinal axis of the device to surround the cavity. In some embodiments, the device further comprises an adhesive disposed between the flexible elongate member and the ultrasound scanner assembly.

According to some aspects of the present disclosure, a method of manufacturing an intraluminal imaging device includes joining a distal portion of a flexible elongate member to a proximal portion of an ultrasound scanner assembly, the ultrasound scanner assembly comprising a plurality of electrical components disposed adjacent to a cavity of the ultrasound scanner assembly, and depositing a coating over and directly contacting the distal portion of the flexible elongate member and a portion of the ultrasound scanner assembly to hermetically seal the cavity of the ultrasound scanner assembly.

In some embodiments, the depositing comprises a vapor deposition process. In some embodiments, the method further includes preparing a surface of the elongate member and a surface of the ultrasound scanner assembly to receive the coating. The preparing the surface includes at least one of a plasma etch, a chemical etch, or an alcohol wipe, in some embodiments. In some embodiments, the method further includes masking, prior to the depositing, at least one of the ultrasound scanner assembly or the flexible elongate member. In some embodiments, the method further includes applying an adhesive between the flexible elongate member and the ultrasound scanner assembly.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5 is a perspective view of a distal portion of an intraluminal imaging device, according to aspects of the present disclosure.

FIG. 6 is a diagrammatic perspective view of a junction disposed on a distal portion of an intraluminal imaging device, according to aspects of the present disclosure.

FIG. 9 is a flow diagram of a method of manufacturing an intraluminal imaging device, according to aspects of the present disclosure.

DETAILED DESCRIPTION

Figure 1:
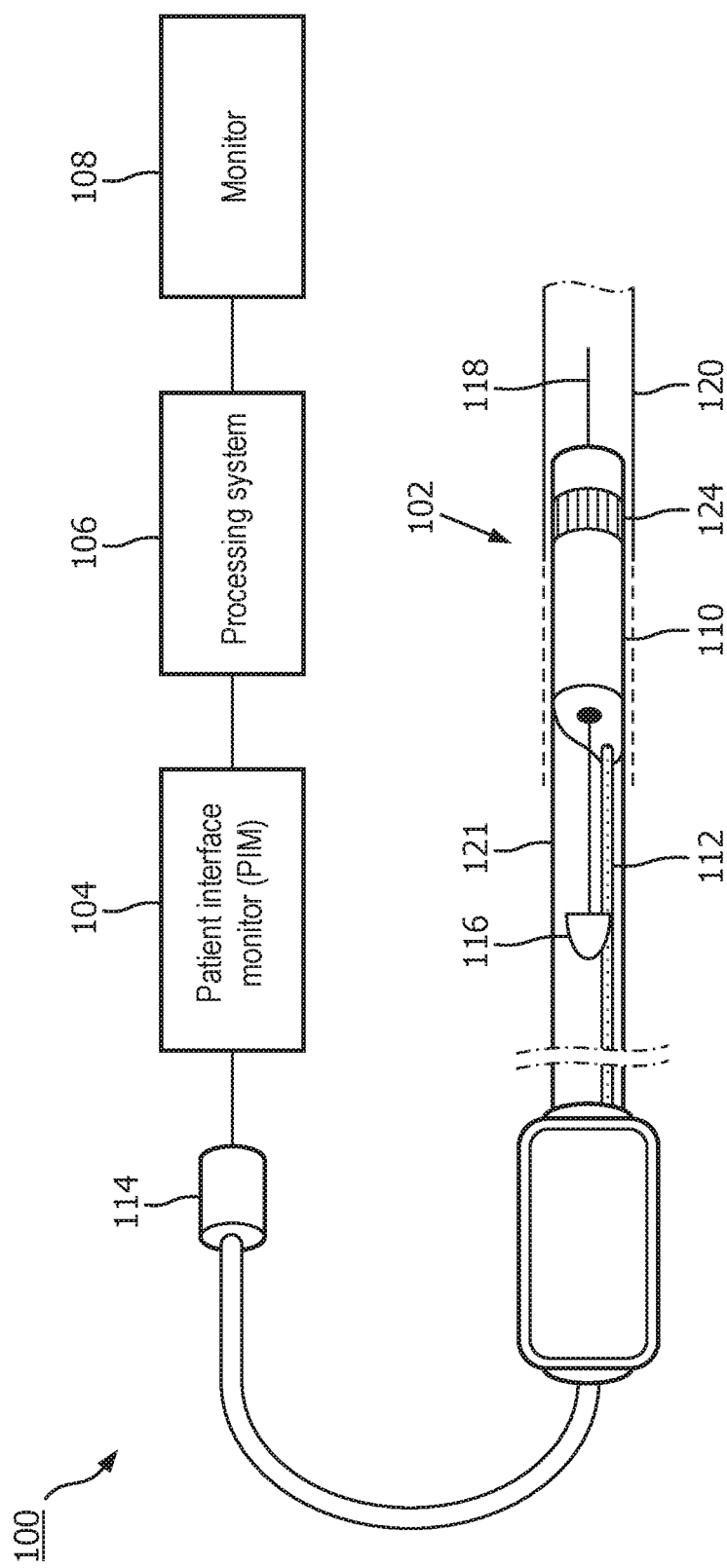
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100, according to aspects of the present disclosure. The intraluminal imaging system 100 can be an ultrasound imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, an processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
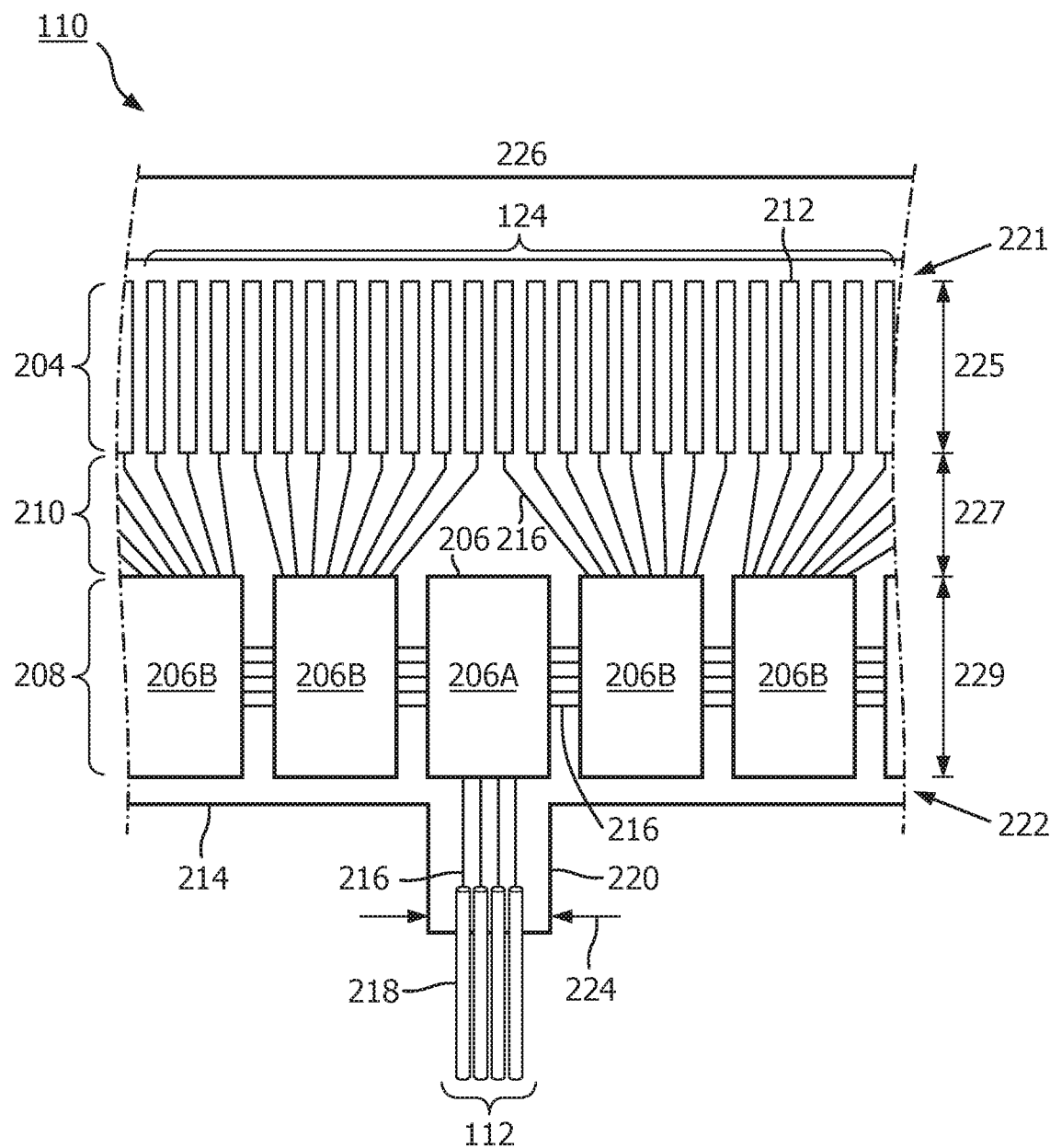
FIG. 2 is a diagrammatic perspective view of the top of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducers 212. The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 μm and 100 μm, with some particular embodiments being between 5 μm and 25.1 μm, e.g., 6 μm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 142 which may serve as an electrical conductor, e.g., electrical conductor 112, between a processing system, e.g., processing system 106, and the flexible assembly 200. Accordingly, the master control circuit may include control logic that decodes control signals received over the cable 142, transmits control responses over the cable 142, amplifies echo signals, and/or transmits the echo signals over the cable 142. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 142 when the conductors 218 of the cable 142 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 μm. For example, in an embodiment, 5 μm conductive traces 216 are separated by 5 μm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 142 are coupled to the flexible substrate 214. For example, the bare conductors of the cable 142 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
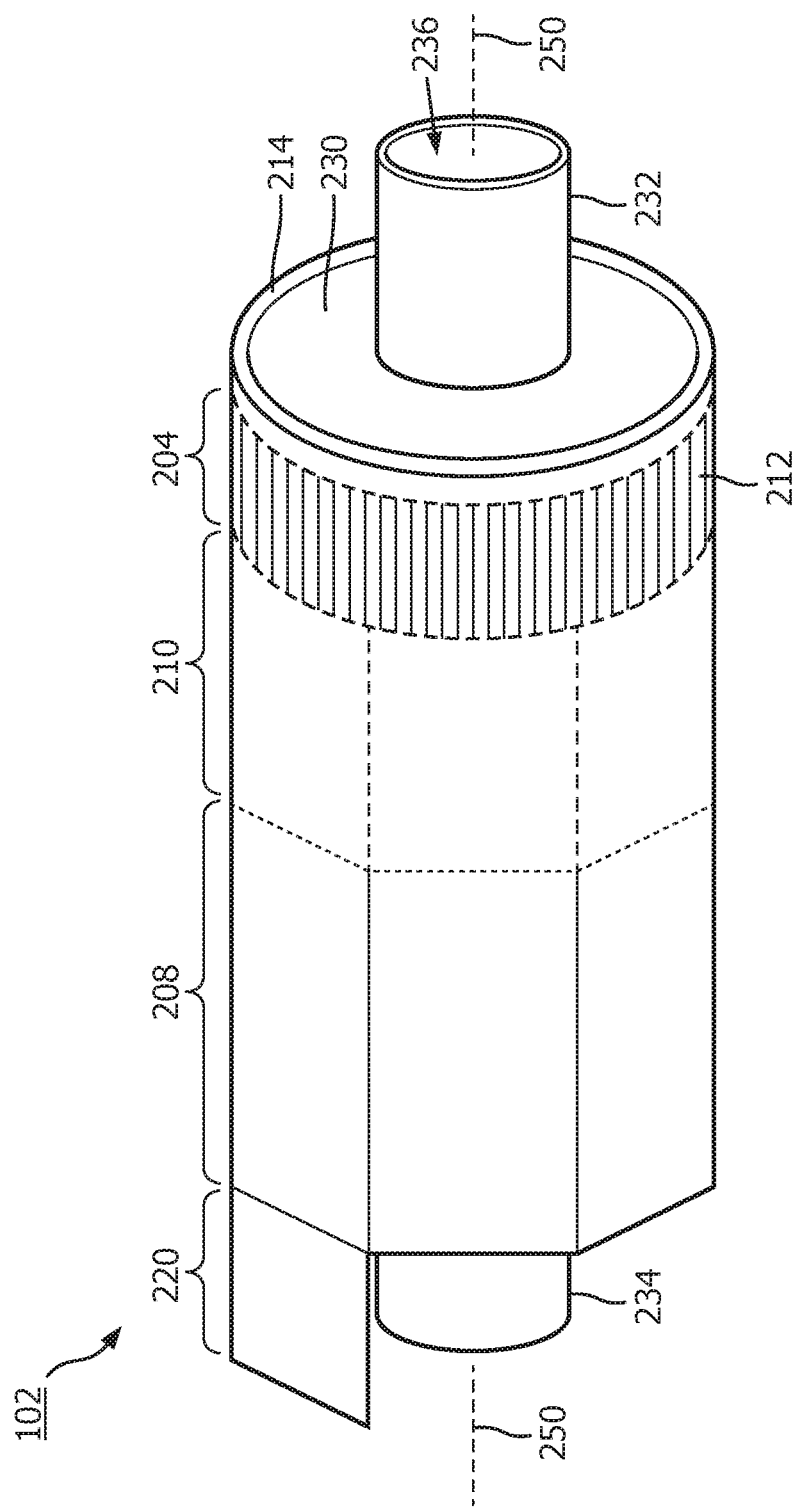
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 110 in a rolled configuration. In some instances, the assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in in an annular configuration, such as a circular configuration or in a polygon configuration, around a longitudinal axis 250 of a support member 230. It will be understood that the longitudinal axis 250 of the support member 230 may also be referred to as the longitudinal axis of the scanner assembly 110, the flexible elongate member 121, and/or the device 102. For example, a cross-sectional profile of the imaging assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 Application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
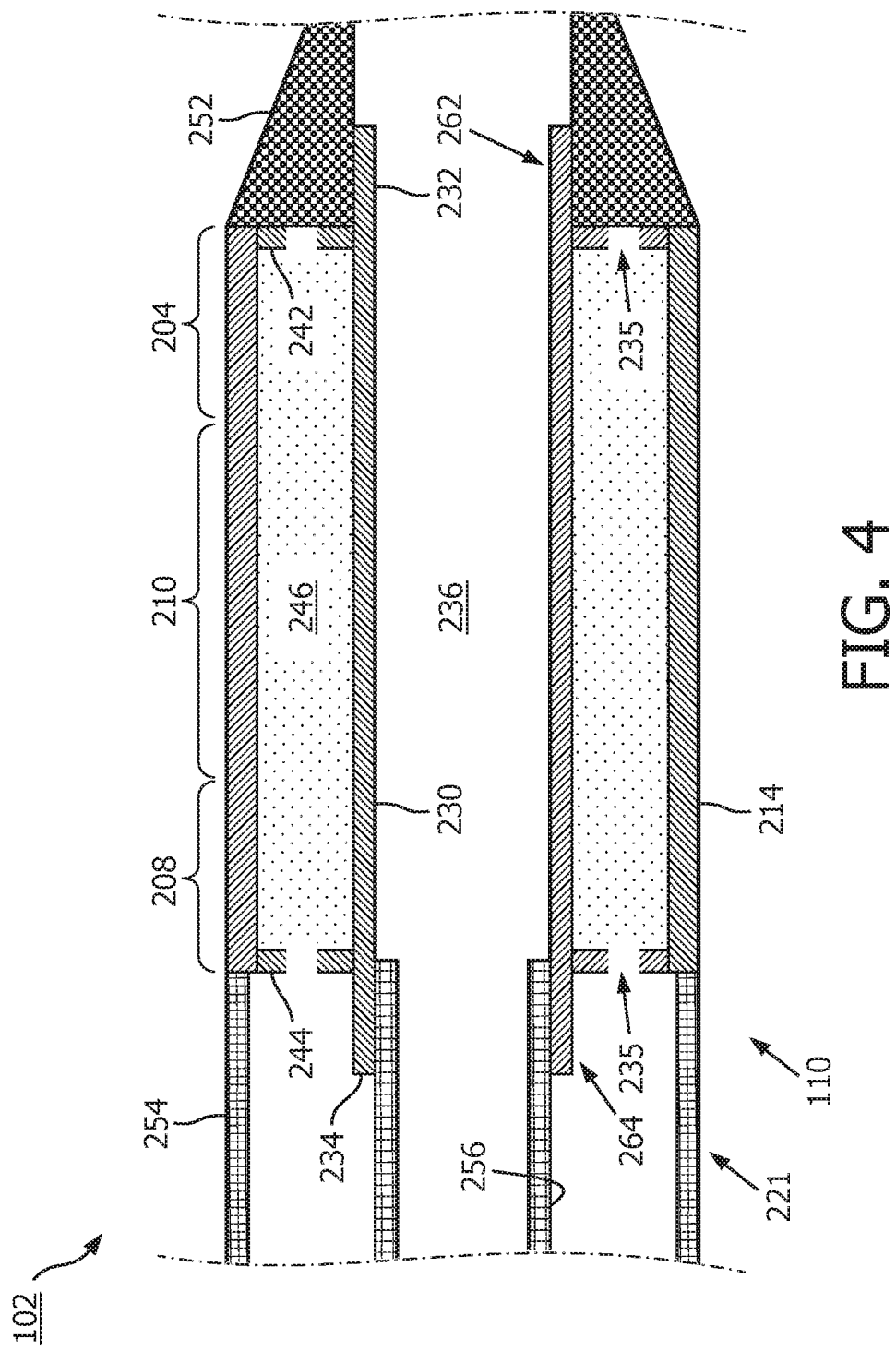
FIG. 4 is a diagrammatic cross-sectional side view of the scanner assembly shown in FIG. 3, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985, 220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion 204 (or transducer region 204), can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive.

FIGS. 5-8 provide various views of an intraluminal imaging device 302, according to some embodiments of the present disclosure. FIG. 5 is a top view of the intraluminal imaging device 302. In some aspects, the device 302 may include similar components as the device 102 shown in FIGS. 1-4. For example, the device 302 includes an ultrasound scanner assembly 310 comprising a flexible substrate 314 wrapped around a support structure 330 that includes a proximal flange 334, and a flexible elongate member 321 joined to the scanner assembly 310 at a junction 348. As described above, the joining of the flexible elongate member 321 and the scanner assembly 310 can be accomplished by applying an adhesive to the components at or near the junction 348, for example. In some embodiments, the joining may be accomplished by an interference fit between for example, a proximal inner member 356 and the proximal flange 334 and/or the flexible substrate 314 and a proximal outer member 354 (FIG. 6). In other embodiments, the joining includes positioning the flexible elongate member 321 to abut the scanner assembly 310. The device 302 further includes a distal member 352 coupled to a distal end of the scanner assembly 310.

FIG. 6 provides a closer view of the intraluminal imaging device 302 shown in FIG. 5. In particular, FIG. 6 shows the junction 348 between the flexible elongate member 321 and the scanner assembly 310. In some embodiments, the junction 348 may comprise a gap or interface between the proximal outer member 354 and the flexible substrate 314. In some instances, the gap at the junction 348 exists because of the transition from a circular cross-sectional profile of distal end 323 of the proximal outer member 354 to the polygonal cross-sectional profile of the proximal end 322 of the flexible substrate 314. Gaps can exist where the different cross-sectional shapes at the junction 348 do not match. In other embodiments, a proximal end 322 of the flexible substrate 314 may receive the distal end 323 of the proximal outer member 354, such that the proximal end 322 of the flexible substrate 314 at least partially overlaps the distal end 323 of the proximal outer member 354. In still other embodiments, the distal end 323 of the proximal outer member 354 may receive the proximal end 322 of the flexible substrate 314, such that the distal end 323 of the proximal outer member 354 at least partially overlaps the proximal end 322 of the flexible substrate 314. In some embodiments, the flexible elongate member 321 and scanner assembly 310 may be held together by a coupling of the proximal inner member 356 and the proximal flange 334 of the support structure 330.

When the flexible elongate member 321 is joined and/or coupled to the scanner assembly 310, there may be one or more fluid ingress paths at or near the junction 348 between the proximal outer member 354 and the flexible substrate 314 that allow for a fluid external to the device 302 to infiltrate various portions of the device 302, in particular the scanner assembly 310, including portions containing exposed electronics. If fluids enter portions of the device 310 containing exposed electronics, the electronics could be damaged and/or electrically shorted. Thus, it may be beneficial to provide a barrier or seal at the junction 348 between the flexible elongate member 321 and the scanner assembly 310, such as between the proximal outer member 354 and the flexible substrate 314 and/or between the proximal outer member 354 and other portions of the scanner assembly 310.

Techniques to seal gaps and interfaces, such as the junction 348, include adhesive bonding, using fillets or potting materials to fill relatively larger gaps, welding or fusing, and jacketing. However, each of these techniques may have drawbacks. For example, although adhesives may provide a sealing connection between the components of the device, adhesives can be difficult to uniformly apply to an IVUS device without significantly increasing its cross-sectional profile. Using fillets and potting materials to fill relatively lager gaps can be challenging and complex from a manufacturing standpoint. Welding or fusing materials together, such as polymers, is not always possible as the different polymers may not be compatible for welding or fusing. In some instances, a tubular jacket or sleeve is placed on and bonded to the device to cover one or more joints or interfaces. However, such jackets can increase complexity of the manufacturing process, and may also increase the cross-sectional profile of the device. Furthermore, each of the methods described above may limit the mobility and/or flexibility of the device, and may fail to provide an adequate, lasting seal throughout the use of the device. As explained in more detail below, a deposited coating 370 positioned over and directly contacting the flexible elongate member 321, the scanner assembly 310, and the junction 348, may overcome some of the drawbacks associated with other sealing methods described above.

Figure 7:
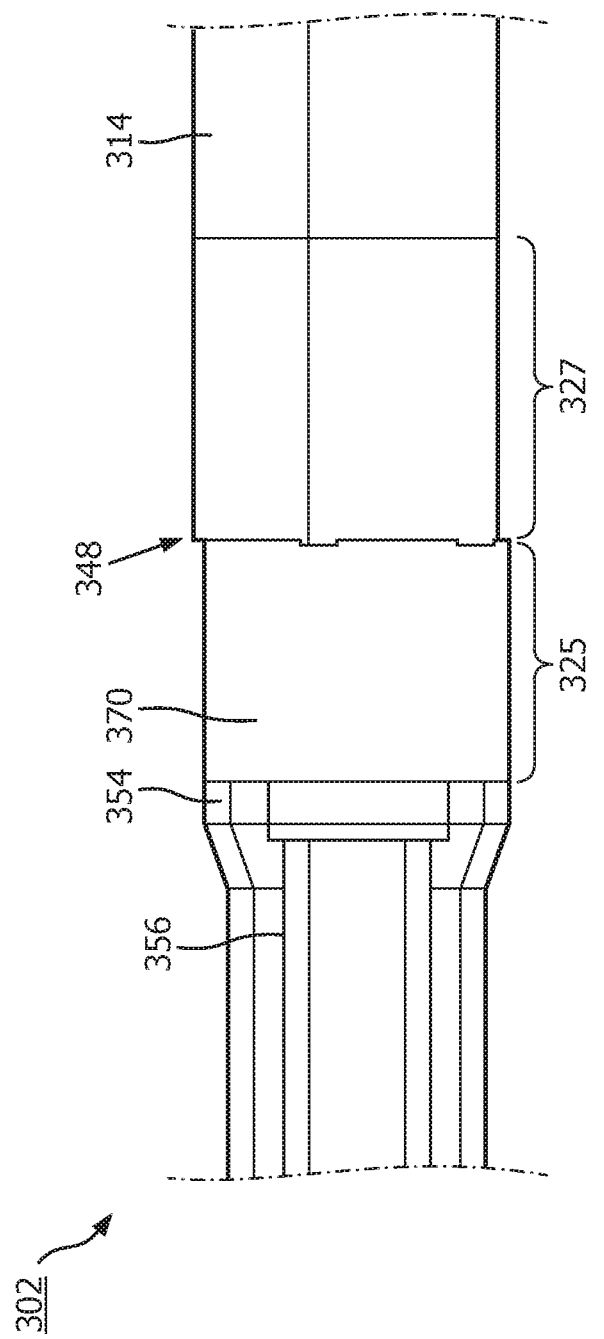
FIG. 7 is a diagrammatic perspective view of the junction of the intraluminal imaging device shown in FIG. 6, with a coating positioned over and surrounding the junction, according to aspects of the present disclosure.

FIG. 7 shows the device 302 with a coating 370, or material layer, deposited over and directly contacting the flexible elongate member 321 and the scanner assembly 310. In particular, the coating 370 is positioned at least partially over and directly contacting a distal portion 325 of the proximal outer member 354 and a proximal portion 327 of the flexible substrate 314. The coating 370 is also positioned over and around the junction 348 to provide a fluid seal or barrier for any internal electronic components.

The coating 370 may be applied by a deposition process, such as a chemical vapor deposition (CVD) process. In other embodiments, the coating 370 can be applied by processes including atomic layer deposition, or any other suitable deposition or application process. The coating 370 may have a thickness ranging from a few nanometers to several micrometers. In some embodiments, the coating 370 has a thickness of less than 0.0005", or less than about 3 microns. By contrast, using a polymer jacket or sleeve results in a thickness of greater than 0.001", or greater than about 25 microns. In some aspects, the coating 370 can comprise a thin film. By maintaining the thickness of the coating 370 to the micron and sub-micron range, the cross-sectional profile of the device 302 can be maintained small and flexible enough to navigate the tortuous vasculature of the patient. Furthermore, the coating 370, which can be applied by a deposition process such as CVD, can mitigate build-up of material at the junction 348 or other edges or surfaces, which is commonly observed when adhesives are used to couple or join components of an intraluminal device. Furthermore, the deposited coating 370 may provide better penetration and coverage in and over the junction 348 to provide improved sealing and reduce or eliminate ingress of fluids into the device 302. Further still, applying the coating 370 by a deposition process may allow for the use of materials that cannot be used in adhesives or jackets, for example.

In some embodiments, the coating 370 may extend over the flexible elongate member 321 and/or the scanner assembly 310 by an amount between about 0.5 mm and about 10 mm. For example, starting from the junction between flexible elongate member 321 and the scanner assembly 310, the coating 370 can extend by any suitable amount proximally to cover at least a portion of the flexible elongate member 321 and/or distally to cover at least a portion of the scanner assembly 310. For example, the coating 370 may extend over flexible elongate member 321 and/or the scanner assembly 310 by 2 mm, 4 mm, 6 mm, 8 mm, or any suitable amount. In other embodiments, the coating 370 may extend over a larger amount of the flexible elongate member 321 and/or the scanner assembly 310, such as between about 5 mm and about 50 mm. In still other embodiments, the coating 370 may extend over all or a substantial portion of the flexible elongate member 321 and/or the scanner assembly 310.

In some embodiments, the coating 370 may comprise a polymer. In some embodiments, the polymer may comprise a hydrophobic material. For example, the coating 370 may comprise parylene. In other embodiments, the coating 370 may comprise a fluoropolymer, such polytetrafluoroethylene (PTFE) or fluorinated ethylene propylene (FEP). In some embodiments, the coating 370 comprises polyethylene naphthalate (PEN). In other embodiments, the coating 370 can comprise an inorganic material, such as aluminum oxide ($AL_2O_3$). In still other embodiments, the coating 370 may provide an acoustic matching layer for the device 302. In that regard, the coating 370 may comprise a material that acoustically matches other materials in or adjacent to an imaging path of an ultrasound transducer to reduce image noise and/or artifacts in an ultrasound image caused by acoustically mismatched materials.

In some embodiments, the coating 370 may include multiple layers of material. Each layer may include a material different from the material of the immediately adjacent layer(s). The material of the coating 370 may be selected or engineered to exhibit certain properties, such as flexibility, elasticity, biocompatibility, strength, etc. The coating 370 can be resilient to cleaning or sterilization techniques, in some embodiments. For example, the coating 370 may be configured to withstand an Ethylene Oxide (EtO) sterilization process.

The coating 370 may be positioned around the junction 348 to seal one or more portions of the scanner assembly 310. In some embodiments, the coating 370 may seal the junction 348 to prevent ingress of fluid from the exterior of the device 302 to an interior of the device. For example, when the scanner assembly 310 is in the rolled configuration as shown in FIG. 7, the scanner assembly 310 may include electronic components (e.g., ultrasound transducers 212, conductive traces 216, controllers 206 of FIG. 2) on the inside of the assembly 310, adjacent to or extending within a cavity 346 formed, created, and/or defined by the rolled scanner assembly 310. Sealing the cavity 346 is thus important to prevent liquid from coming in contact with, damaging, and/or shorting out the electronic components. The coating 370 may be used as the sole means of sealing the junction 348 in some embodiments. In other embodiments, the coating 370 may be used in conjunction with one or more sealing options, such as adhesives, fillets or potting, and jackets. For example, in some embodiments, the coating 370 may be applied to the junction 348 after an adhesive is used at the junction to join the flexible elongate member 321 and the scanner assembly 310.

Figure 8:
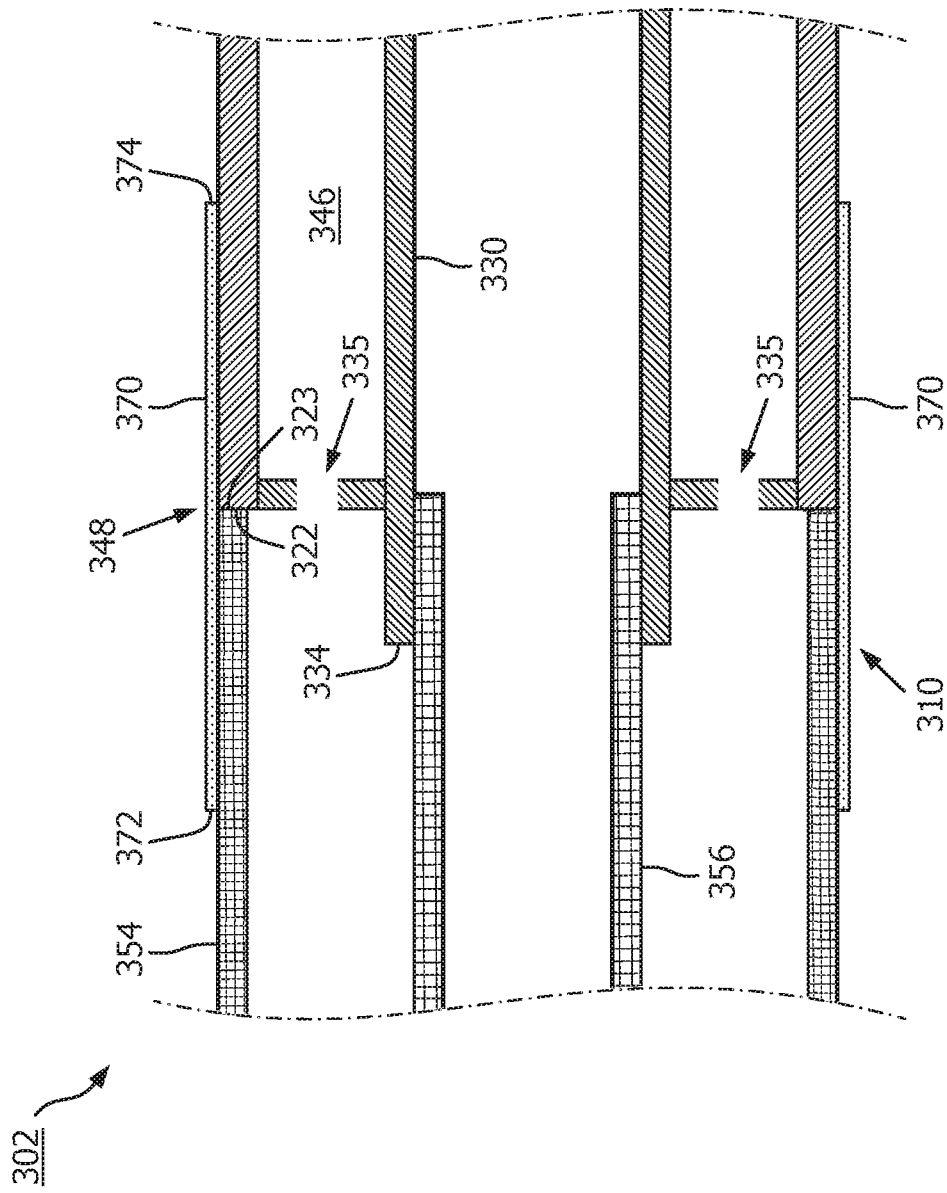
FIG. 8 is a diagrammatic cross-sectional side view of the junction of the intraluminal imaging device shown in FIG. 7, according to aspects of the present disclosure.

Although the coating 370 is shown in FIGS. 7 and 8 as positioned over and surrounding the junction 348 between the flexible elongate member 321 and the scanner assembly 310, the present disclosure also contemplates depositing coatings at other portions, junctions, voids, interfaces, etc. of the device 302 or other intraluminal devices. For example, a coating could be deposited over one or more portions, junctions, voids, interfaces, etc. of a rotational IVUS device, optical coherence tomography (OCT) device, pressure-sensing catheter, pressure-sensing guidewire, intracardiac echocardiography (ICE) device, RF ablation device, or any other suitable device.

FIG. 8 provides a diagrammatic cross-sectional side view of the junction 348 of the device 302 shown in FIG. 7. Similar to the cross-sectional view shown in FIG. 4, the device 302 includes the proximal outer member 354 and proximal inner member 356 joined to the ultrasound scanner assembly 310. The proximal inner member 356 is received by the flange 334 of the support structure 330, and the proximal outer member 354 abuts the proximal end 322 of the flexible substrate 314. The coating 370 is positioned over and directly contacting the distal portion 325 of the proximal outer member 354 and the proximal portion 327 of the flexible substrate 314. The coating 370 is also positioned over and around the junction 348, to provide a barrier between the exterior of the device 302 and one or more interior portions of the device 302, such as the cavity 346. If the coating 370 were not applied to the junction 348, fluids could enter the interior of the device 320, such as the cavity 346, thereby compromising any exposed electronic components adjacent the cavity 346.

The coating 370 includes a first masking line 372 forming a boundary of the coating 370 at a proximal end of the coating 370 and a second masking line 374 forming a boundary of the coating 370 at a distal end of the coating 370. The masking lines 372, 374, can be formed by applying a masking material before the coating 370 is deposited, as described below. Although the first and second masking lines 372, 374, are shown near the junction 348, in other embodiments, one or more of the masking lines may be closer to, or further from, the junction 348. In some embodiments, the coating 370 may include the first masking line 372, but not the second masking line 374, or vice versa. For example, in some embodiments, the coating 370 may be positioned over the entire scanner assembly 310, or a large portion of the scanner assembly 310. For example, the coating 370 may be positioned around a large portion of the scanner assembly, including the junction, and the ultrasound transducers. In embodiments wherein the coating is positioned around the transducers, it may be advantageous for the coating 370 to include an acoustically matched material to maintain the quality and integrity of the obtained ultrasound images. In other embodiments, the coating 370 may be positioned around a portion of the proximal outer member 354, or the entire proximal outer member 354. In that regard, in some embodiments, the coating 370 may not have a first masking line 372 or a second masking line 374.

FIG. 9 is a flow diagram showing steps involved in a method 400 of manufacturing an intraluminal imaging device, according to some aspects of the present disclosure. At step 410, the ultrasound scanner assembly, which may also be described as a flex circuit comprising a flexible substrate, is wrapped around the support structure, or unibody. The scanner assembly may be joined to the support structure by welding and/or using adhesives. As described above, the support structure may have a cylindrical profile. The scanner assembly, which includes a plurality of electronic components mounted on a flexible substrate, may adopt a circular profile similar to the support structure in the rolled configuration. However, as also described above, the scanner assembly may adopt a polygonal profile, such as a nonagon.

At step 420, the distal portion of the flexible elongate member and the proximal portion of the scanner assembly are joined together at a junction. The flexible elongate member can include a proximal outer member and a proximal inner member as described above. In some embodiments, the step of joining the flexible elongate member and scanner assembly includes using adhesives, tapes, or other means of temporarily or permanently coupling the flexible elongate member and the scanner assembly. For example, the proximal inner member can be inserted into the proximal flange of the support structure. The proximal inner member may be held in place by an interference between the proximal inner member and the proximal flange and/or by adhesives. The proximal outer member may then be moved, slid, or translated distally with respect to the proximal inner member such that the distal end of the proximal outer member abuts the proximal end of the flexible substrate of the scanner assembly. In other embodiments, the step of joining comprises positioning the distal portion of the flexible elongate member near the proximal portion of the scanner assembly. Fixtures, mandrels, or jigs may be used to maintain the flexible elongate member and the scanner assembly in place and joined together for one or more steps of the method 400.

At step 430, one or more surfaces of the flexible elongate member and/or the scanner assembly are prepared for the deposition process. The step of preparing shown in step 430 may include one or more of: a cleaning process; an alcohol wipe; a chemical etch; a plasma etch; or any other suitable process that prepares the one or more surfaces to receive a coating by a deposition process. Although the step 430 is shown as following step 420, in some embodiments, the surface preparation process can be performed before or after many of the steps of the method 400. For example, the surfaces can be prepared before step 410, before step 420, or after step 440.

At step 440, a masking material is applied to one or more surfaces of the scanner assembly and/or the flexible elongate member to define corresponding coated and uncoated regions on the device. For example, a masking shield, sleeve, or tape, may be applied to the uncoated regions of the device. The masking material may comprise edges, such as a distal edge and a proximal edge that form or define one or more masking lines at the ends or edges of the coating. The masking material can be applied to both the proximal outer member and the flexible substrate to establish or define an unmasked, or coated portion, and a masked, or uncoated portion. In other embodiments, the masking material may be applied to only one of the At step 450, the coating is deposited to the device to coat the unmasked, or coated regions of the device. The depositing can include a deposition process, such as a chemical deposition process, an atomic layer deposition process, or any other suitable process. In some embodiments, the coating is deposited around one or more perimeters (e.g., circumferences) of the device. In other embodiments, the coating does not completely circumscribe the device. In some embodiments, step 450 may include depositing multiple layers of material. Each layer may comprise a material different from the adjacent layer(s).

The method 400 shown in FIG. 9 may include fewer or more steps than those illustrated. For example, in some embodiments, the method 400 includes applying an adhesive or fillet to the junction of the device before depositing the coating. In some embodiments, the method includes removing the masking material after the coating is deposited in step 450. In other embodiments, the surface preparation step 430 is not performed. It is also contemplated by the present disclosure that the order or arrangement of the steps of the method 400 can be otherwise changed.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
   a catheter configured to be positioned within a body lumen of a patient, the catheter comprising a proximal portion, a distal portion, and an exterior surface;
   a flex circuit comprising a proximal portion, a distal portion, an exterior surface, an interior surface, and a plurality of electrical components disposed on the interior surface, wherein the flex circuit defines a cavity, wherein the plurality electrical components are disposed adjacent to the cavity, wherein the proximal portion of the flex circuit is coupled to the distal portion of the catheter; and
   a coating extending over a location where the proximal portion of the flex circuit is coupled to the distal portion of the catheter, wherein the coating is separate from the flex circuit and the catheter, wherein the coating is disposed outside of the flex circuit and the catheter, wherein the coating directly contacts both the exterior surface of the distal portion of the catheter and the exterior surface of the proximal portion of the flex circuit such that the coating hermetically seals the cavity, wherein the coating comprises a proximal boundary at the distal portion of the catheter, a distal boundary at the flex circuit, and a continuous length between the proximal boundary and the distal boundary, wherein the continuous length overlaps the location where the proximal portion of the flex circuit is coupled to the distal portion of the catheter.

2. The device of claim 1, wherein the coating is deposited directly over the distal portion of the catheter and the proximal portion of the flex circuit.

3. The device of claim 1, wherein the coating comprises a hydrophobic material.

4. The device of claim 1, wherein the coating comprises parylene.

5. The device of claim 1, wherein the coating comprises a thickness of less than 3 microns.

6. The device of claim 1, wherein the distal boundary is at the proximal portion of the flex circuit.

7. The device of claim 1, wherein the coating is deposited around perimeters of the catheter and the flex circuit.

8. The device of claim 1,
   wherein the plurality of electrical components comprises one or more acoustic elements, and
   wherein the coating comprises an acoustic matching layer positioned over the one or more acoustic elements.

9. The device of claim 1,
   wherein the flex circuit comprises a flexible substrate including a proximal portion and a distal portion, and
   wherein the flexible substrate is positioned around a longitudinal axis of the device to surround the cavity.

10. The device of claim 1, further comprising an adhesive disposed between the catheter and the flex circuit.

11. The device of claim 1, wherein the flex circuit is positioned around a longitudinal axis of the device to surround the cavity.

12. The device of claim 11, wherein a cross section of the catheter is circular and a cross section of the flex circuit is polygonal.

13. The device of claim 11, further comprising:
   an inner member disposed within the catheter; and
   a support member disposed within the cavity.

14. The device of claim 13, wherein a proximal end of the support member comprises a flange.

15. The device of claim 14, wherein the inner member is receivable in the flange of the support member.

16. An intravascular ultrasound imaging (IVUS) device, comprising:
   a catheter configured to be positioned within a vessel of a patient;
   a flex circuit arranged around a longitudinal axis of the catheter to form a cavity, wherein the flex circuit comprises a proximal portion coupled to a distal portion of the catheter;
   a plurality of electrical components coupled to the flex circuit adjacent to the cavity; and
   a coating extending over a location where the proximal portion of the flex circuit is coupled to the distal portion of the catheter to prevent ingress of fluid into the cavity, wherein the coating is separate from the flex circuit and the catheter, wherein the coating is disposed outside of the flex circuit and the catheter, wherein the coating directly contacts both an exterior surface of the distal portion of the catheter and an exterior surface of the proximal portion of the flex circuit, wherein the coating comprises a proximal boundary at the distal portion of the catheter, a distal boundary at the flex circuit, and a continuous length between the proximal boundary and the distal boundary, wherein the continuous length overlaps the location where the proximal portion of the flex circuit is coupled to the distal portion of the catheter.

17. The device of claim 16, wherein the coating comprises a hydrophobic material.

18. The device of claim 16, wherein portions of the coating directly contacting the exterior surface of the distal portion of the catheter and the exterior surface of the proximal portion of the flex circuit have a thickness of less than 3 microns.

19. The device of claim 16, wherein the distal boundary is at the proximal portion of the flex circuit.

20. The device of claim 16,
   wherein the plurality of electrical components comprises one or more acoustic elements, and
   wherein the coating comprises an acoustic matching layer positioned over the one or more acoustic elements.

* * * * *